(12) United States Patent
Ando et al.

(10) Patent No.: US 9,011,582 B2
(45) Date of Patent: Apr. 21, 2015

(54) OXYGEN ENRICHMENT DEVICE

(75) Inventors: Makoto Ando, Yamaguchi (JP); Hisashi Kiriake, Yamaguchi (JP)

(73) Assignee: Teijin Pharma Limited, Tokyo (JP)

( * ) Notice: Subject to any disclaimer, the term of this patent is extended or adjusted under 35 U.S.C. 154(b) by 420 days.

(21) Appl. No.: 13/505,242

(22) PCT Filed: Oct. 29, 2010

(86) PCT No.: PCT/JP2010/069766
§ 371 (c)(1),
(2), (4) Date: Jul. 9, 2012

(87) PCT Pub. No.: WO2011/052803
PCT Pub. Date: May 5, 2011

(65) Prior Publication Data
US 2012/0272966 A1 Nov. 1, 2012

(30) Foreign Application Priority Data

Nov. 2, 2009 (JP) .................................. 2009-252056

(51) Int. Cl.
*A61M 16/10* (2006.01)
*B01D 53/047* (2006.01)
*B01D 53/30* (2006.01)
(Continued)

(52) U.S. Cl.
CPC ....... *A61M 16/10* (2013.01); *A61M 2202/0208* (2013.01); *B01D 53/047* (2013.01); *B01D 53/30* (2013.01); *B01D 2253/108* (2013.01); *B01D 2256/12* (2013.01); *B01D 2257/102* (2013.01); *B01D 2259/40043* (2013.01); *B01D 2259/402* (2013.01); *B01D 2259/4533* (2013.01); *A61M 16/16* (2013.01); *A61M 2016/0039* (2013.01); *A61M 2016/1025* (2013.01); *A61M 2205/3368* (2013.01); *A61M 16/101* (2014.02)

(58) Field of Classification Search
USPC ........ 95/8, 12, 14, 23, 130; 96/110–112, 116, 96/121; 128/204.18, 205.12, 205.27
See application file for complete search history.

(56) References Cited

U.S. PATENT DOCUMENTS

| 5,529,607 | A | * | 6/1996 | Tan | .................................. | 95/12 |
| 6,102,985 | A | * | 8/2000 | Naheiri et al. | .................. | 95/101 |
| 8,142,544 | B2 | * | 3/2012 | Taylor et al. | ...................... | 95/22 |
| 8,608,827 | B2 | * | 12/2013 | Haberland et al. | ................ | 95/23 |
| 2005/0045041 | A1 | * | 3/2005 | Hechinger et al. | ............. | 96/121 |

FOREIGN PATENT DOCUMENTS

| EP | 1440935 A1 | 7/2004 |
| EP | 2210640 A1 | 7/2010 |

(Continued)

OTHER PUBLICATIONS

Extended Search Report issued in European Application No. 10826932.5, dated Feb. 7, 2014.

(Continued)

*Primary Examiner* — Frank Lawrence
(74) *Attorney, Agent, or Firm* — Rader, Fishman & Grauer PLLC

(57) ABSTRACT

Disclosed is an oxygen enrichment that can follow changes in adsorption performance in response to changes in the temperature of the usage environment and can reduce power consumption. The oxygen enrichment device has a purge step control means that controls a purge step time to increase/decrease the length of a purge step so as to maximize the oxygen concentration by changing opening/closing timing of a flow-channel switching means while the oxygen enrichment device is running.

11 Claims, 4 Drawing Sheets

(51) Int. Cl.
*A61M 16/16* (2006.01)
*A61M 16/00* (2006.01)

(56) References Cited

FOREIGN PATENT DOCUMENTS

| JP | 2002-253675 A | 10/2002 |
|---|---|---|
| JP | 2006-141896 A | 6/2006 |
| JP | 2007-000340 A | 11/2007 |
| JP | 2008-125885 A | 6/2008 |
| WO | WO-02/11861 A1 | 2/2002 |
| WO | WO-2008/027728 A1 | 3/2008 |
| WO | WO-2010/073140 A2 | 7/2010 |

OTHER PUBLICATIONS

Communication pursuant to Article 94(3) EPC issued in European Application No. 10826932.5, dated Mar. 6, 2014.
International Search Report mailed Nov. 30, 2010.

* cited by examiner

FIG. 2

| Adorption cylinder 131 | Pressure equalizing step | Desorption step | Purge step | Pressure equalizing step | Adsorption step | Purge step |
|---|---|---|---|---|---|---|
| Adorption cylinder 132 | Pressure equalizing step | Adsorption step | Purge step | Pressure equalizing step | Desorption step | Purge step |

Length of purge step

OXYGEN ENRICHMENT DEVICE

TECHNICAL FIELD

The present invention relates to a pressure swing adsorption-type oxygen enrichment device using an adsorbent which preferentially adsorbs nitrogen relative to oxygen. More specifically, the present invention relates to a medical oxygen enrichment device used for oxygen inhalation therapy which is performed for a patient with chronic respiratory disease and the like.

BACKGROUND ART

In recent years, the number of patients suffering from respiratory system diseases such as asthma, pulmonary emphysema, chronic bronchitis and the like has tended to increase. One of the most effective therapeutic methods for these diseases is oxygen inhalation therapy. Such oxygen inhalation therapy is that oxygen gas or oxygen-enriched air is inhaled to patients. An oxygen enrichment device separating oxygen from the air, an oxygen supply device using liquid oxygen or oxygen gas cylinder, and the like are known as an oxygen supply source used for oxygen inhalation therapy. However, an oxygen enrichment device is mainly used for home oxygen therapy because it is convenient to use and easy for maintenance and management.

An oxygen enrichment device is a device to supply oxygen by separating and concentrating oxygen that makes up 21% of the air. As such device, there are a membrane-type oxygen enrichment device that uses an oxygen enrichment membrane which selectively permeate oxygen and a pressure swing adsorption-type oxygen enrichment device that uses an adsorbent which selectively adsorbs nitrogen or oxygen. A pressure swing adsorption-type oxygen enrichment device is mainly used because of a benefit of obtaining high oxygen concentration of 90% or more.

The pressure swing adsorption-type oxygen enrichment device continuously produces a highly concentrated oxygen gas by repeating an adsorption step and a desorption step. In the adsorption step in which un-adsorbed oxygen-enriched gas is obtained, nitrogen is adsorbed under pressurized conditions on an adsorbent which selectively adsorbs nitrogen relative to oxygen such as 5A, 13X, Li-X type molecular sieve zeolites filled in an adsorption cylinder to which compressed air is supplied by a compressor. In the desorption step in which the adsorbent is regenerated, nitrogen adsorbed on the adsorbent is desorbed by reducing the pressure in the adsorption cylinder to atmospheric pressure or less by evacuation.

PRIOR ART DOCUMENTS

Patent Documents

Patent Document 1: Japanese Unexamined Patent Application Publication No. 2006-141896
Patent Document 2: Japanese Unexamined Patent Application Publication No. 2002-253675

SUMMARY OF THE INVENTION

Problems to be Solved by the Invention

In the pressure swing adsorption-type oxygen enrichment device using an adsorbent, when raw material air supply volume from a compressed air supply means such as a compressor and the like and an adsorption process sequence are constant, the oxygen concentration of the obtained product gas generally changes depending on environmental temperature and supplied air temperature. This depends on temperature characteristics of the adsorbent relating to selective adsorption ratio of nitrogen or oxygen. As for molecular sieve zeolites such as Li-X type, MD-X type and the like, when the environmental temperature is high, amount of nitrogen adsorbed by the adsorbent is decreased. And thus nitrogen breakthrough occurs in the adsorption step to decrease the product oxygen concentration when a sequence optimized at room temperature is used. When the environmental temperature is low, the nitrogen adsorption ratio of the adsorbent increases. However, the oxygen concentration of the product gas decreases due to insufficient nitrogen desorption, because the nitrogen adsorption rate is decreased in the desorption step.

In recent years, as shown in Patent Document 1, a method has been proposed in which highly concentrated oxygen is secured by changing capacity of a compressed air supply means such as a compressor and the like in response to surrounding environmental temperature. However, since pressure of the air to be introduced into the adsorption cylinder is required to be as high as possible in an oxygen enrichment device using such method, a problem of causing increase in power consumption of the device arises associated with increase in the capacity of compressed air supply of the compressor.

When such medical oxygen enrichment device is used at home, as a bill for electric power necessary to operate the device is charged to a patient, the power consumption is strongly required to be decreased.

In order to lower the power consumption for a pressure swing adsorption-type oxygen enrichment device, a method has been proposed for detecting the concentration of a product gas (oxygen gas) and controlling rotation rate of an electric motor used as an air supply means in response to the detected results (Patent Document 2).

Patent Document 2 describes a pressure swing adsorption-type oxygen enrichment device which realizes a low electric power consumption by changing the supply capacity of a compressed air supply means such as a compressor and the like in response to the detected value of an oxygen-enriched gas of an oxygen concentration detection means. However, as in the device described in Patent Document 1, compression capacity of the compressed air supply means is required to be increased when the environmental temperature is changed, and thus a problem arises, for example, such that an increase in the power consumption of the device is required.

In such device, by controlling the rotation rate of an electric motor to maintain the oxygen concentration at a certain value, lower power consumption is realized at an operation stage earlier than a conventional oxygen enrichment device: namely, when the oxygen production capacity is high because of favorable operational environment or favorable conditions of component parts of the device, power consumption is reduced by suppressing the capacity of the air supply means, and when the oxygen production capacity becomes lowered because of worsening of the operational environment of the device due to, for example, high temperature, cold temperature and the like, or because of deterioration of the component parts of the device, the supply performance of the air supply means is increased. However, it was difficult to maintain production of highly concentrated oxygen in response to changes of the adsorption performance of the adsorbent due to the change in the environmental temperature, only by controlling the air supply means. It was also difficult to achieve substantially lower power consumption.

Means for Solving the Problems

To solve such problems, the present inventors found the present invention described below.

An object of the present invention is to provide a pressure swing adsorption-type oxygen enrichment device comprising:
a plurality of adsorption cylinders filled with an adsorbent which selectively adsorbs nitrogen relative to oxygen;
a compressor for supplying raw material air to the adsorption cylinders;
an adsorption step for supplying compressed air to each of the adsorption cylinders and extracting an oxygen-enriched gas by sequentially switching flow channels between the compressor and each of the adsorption cylinders;
a desorption step for depressurizing each of the adsorption cylinders and regenerating the adsorbent;
a pressure equalizing step for communicating each of the adsorption cylinders;
a flow-channel switching means for repeating a purge step in a specific timing, in which highly concentrated oxygen from the adsorption cylinder in the adsorption step is introduced into the adsorption cylinder in the desorption step;
a flow setting means for supplying the oxygen-enriched gas to a user at a specific flow rate;
an oxygen concentration sensor for detecting an oxygen concentration of the oxygen-enriched gas produced by the oxygen enrichment device;
a temperature sensor for measuring a temperature of the device; and
a purge step control means which controls a length of a purge step so as to maximize the oxygen concentration by changing opening/closing timing of the flow-channel switching means, when an output value of the oxygen concentration sensor is lower than a specified value, or the output value of the temperature sensor is out of a specific temperature range.

Another object of the present invention is to provide the oxygen enrichment device having such purge step control means, wherein:
an oxygen concentration of the oxygen-enriched gas just before a control for changing the length of a purge step is started is used as a reference concentration,
a control for increasing the length of a purge step by a specific length and detection of the oxygen concentration after the control are performed,
the reference concentration is replaced by the oxygen concentration after the change of the length of a purge step if the oxygen concentration is increased, and
controls for increasing the length of a purge step and detection of the oxygen concentration are repeated until the oxygen concentration is decreased compared to the reference concentration (this point is referred to as $P^1$ point below);
the oxygen concentration at $P^1$ point is used as a reference concentration,
a control for decreasing the length of a purge step by a specific length and detection of the oxygen concentration after the control are performed,
the reference concentration is replaced by the oxygen concentration after the change of the length of a purge step if the oxygen concentration is increased, and
controls for decreasing the length of a purge step and detection of the oxygen concentration are repeated until the oxygen concentration is decreased compared to the reference concentration (this point is referred to as $Q^1$ point below);
the oxygen concentration at $Q^1$ point is used as a reference concentration,
a control for increasing the length of a purge step by a specific length and detection of the oxygen concentration after the control are performed,
the reference concentration is replaced by the oxygen concentration after the change of the length of a purge step if the oxygen concentration is increased, and
controls for increasing the length of a purge step and detection of the oxygen concentration are repeated until the oxygen concentration is decreased compared to the reference concentration (this point is referred as $R^1$ point below); and
the midpoint between points $Q^1$ and $R^1$ is determined as an optimal length of a purge step.

Another object of the present invention is to provide the oxygen enrichment device having such purge step control means, wherein:
an oxygen concentration of the oxygen-enriched gas just before a control for changing the length of a purge step is started is used as a reference concentration,
a control for decreasing the length of a purge step by a specific length and detection of the oxygen concentration after the control are performed,
the reference concentration is replaced by the oxygen concentration after the change of the length of a purge step if the oxygen concentration is increased, and
controls for decreasing the length of a purge step and detection of the oxygen concentration are repeated until the oxygen concentration is decreased compared to the reference concentration (this point is referred as $P^2$ point below);
the oxygen concentration at $P^2$ point is used as a reference concentration,
a control for increasing the length of a purge step by a specific length and detection of the oxygen concentration after the control are performed,
the reference concentration is replaced by the oxygen concentration after the change of the length of a purge step if the oxygen concentration is increased, and
controls for increasing the length of a purge step and detection of the oxygen concentration are repeated until the oxygen concentration is decreased compared to the reference concentration (this point is referred as $Q^2$ point below);
the oxygen concentration at the $Q^2$ point is used as a reference concentration,
a control for decreasing the length of a purge step by a specific length and detection of the oxygen concentration after the control are performed,
the reference concentration is replaced by the oxygen concentration after the change of the length of a purge step if the oxygen concentration is increased, and
controls for decreasing the length of a purge step and detection of the oxygen concentration are repeated until the oxygen concentration is decreased compared to the reference concentration (this point is referred as $R^2$ point below); and
the midpoint between points $Q^2$ and $R^2$ is determined as an optimal length of a purge step.

Another object of the present invention is to provide the oxygen enrichment device having such purge step control means, wherein:
an output value of the temperature sensor at the time of startup of the oxygen enrichment device or at the time of change in a set flow rate is registered as a reference temperature, and the length of a purge step determined by the reference temperature is set/controlled as a default value, and
an output value of the temperature sensor at the time of startup of the oxygen enrichment device or at the time of change in a set flow rate is registered as a reference temperature, the length of a purge step is reset to a length of a purge step that is predetermined based on the output value of the temperature sensor when the detected value of the temperature sensor is changed more than a specified value compared to the reference temperature.

Another object of the present invention is to provide the oxygen enrichment device having such purge step control means provided with a preset range in which the length of a purge step is variable, wherein:
if the length of a purge step reaches a limit of the range in which the length of a purge step is variable without detecting a P point at which the oxygen concentration is decreased compared to the reference concentration, or
if the length of a purge step reaches a limit of the range in which the length of a purge step is variable without detecting a Q point at which the oxygen concentration is decreased compared to the reference concentration after detecting the P point,
the attained limit of the range in which the length of a purge step is variable is determined as an optimal length of a purge step.

Another object of the present invention is to provide the oxygen enrichment device having an oxygen flow rate sensor for detecting a flow rate of the oxygen-enriched gas produced by the oxygen enrichment device, wherein
the purge step control means performs control for stopping or suspending of executing the change of the length of a purge step when the flow rate of the oxygen-enriched gas is out of a specific range or when the detected value of the temperature sensor is out of a specific range of variation.

Effect of the Invention

According to the present invention, an optimal operation sequence can be provided, which is constantly capable of producing a highly concentrated enriched oxygen gas in response to change in adsorption efficiency of the adsorbent depending on the temperature change of the usage environment of the oxygen enrichment device. The present invention provides the device capable of supplying oxygen in a stable manner for a user with low power consumption.

BRIEF DESCRIPTION OF DRAWINGS

FIG. 2 is a schematic diagram showing each step according to an example of the oxygen enrichment device of the present invention.

BEST MODE FOR CARRYING OUT THE PRESENT INVENTION

Figure 1:
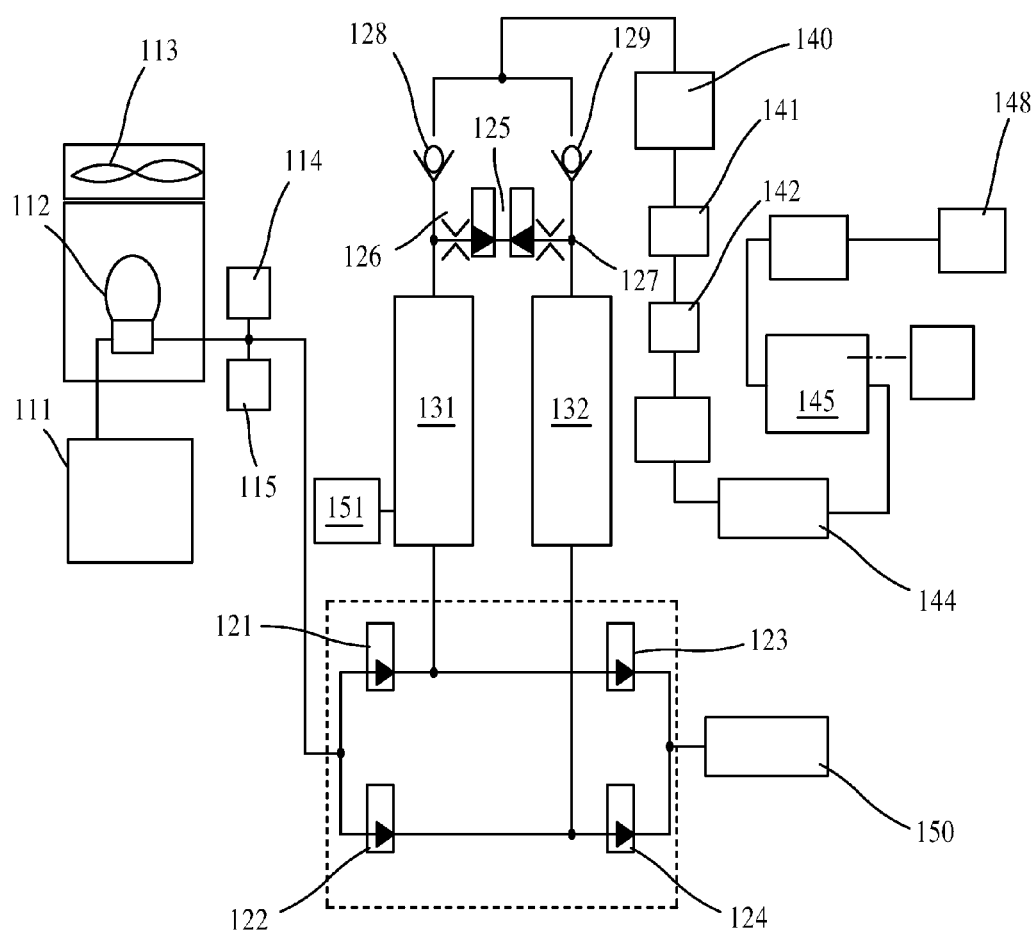
FIG. 1 is a schematic diagram showing a pressure swing adsorption-type oxygen enrichment device according to an example of the oxygen enrichment device of the present invention.

An example of an oxygen enrichment device of the present invention will be described with reference to the drawings below.
FIG. 1 is a schematic constitutional diagram showing the pressure swing adsorption-type oxygen enrichment device according to one embodiment of the present invention. A pressure swing adsorption-type oxygen enrichment device 1 according to the present invention has a compressor 112 which supplies raw material air, adsorption cylinders 131 and 132 filled with adsorbents that selectively adsorb nitrogen relative to oxygen, supply valves 121 and 122 that are flow-channel switching means for switching between adsorption and desorption steps, exhaust valves 123 and 124, and a pressure equalizing valve 125. An oxygen-enriched gas that is separated and generated from the raw material air is regulated to a specific flow rate using a flow meter (a control valve 142), and supplied to a user using a cannula 148.

Raw material air brought into the oxygen enrichment device from the outside is first taken in an air intake port having an external air intake filter 111 and the like to eliminate foreign matter such as dust and the like. At this time, normal air contains about 21% oxygen gas, about 77% nitrogen gas, 0.8% argon gas, and 1.2% other gas such as carbon dioxide and the like. Such oxygen enrichment device separates, concentrates, and isolates an oxygen gas required as a breathing gas.

In an adsorption step, compressed air from the compressor 112 is sequentially supplied to the adsorption cylinders 131 and 132 filled with the adsorbents containing zeolites and the like that selectively adsorb nitrogen gas molecules relative to oxygen gas molecules by switching a flow channel for supplying raw material air to a targeted adsorption cylinder, by controlling opening/closing of the supply valves 121 and 122 and the exhaust valves 123 and 124. Then in the adsorption cylinders 131 and 132 that are in a pressurized state, about 77% nitrogen gas contained in the raw material air is selectively adsorbed and eliminated to isolate the oxygen-enriched gas.

Such adsorption cylinders are composed of cylindrical vessels filled with adsorbents that selectively adsorb nitrogen relative to oxygen. The number of adsorption cylinders is decided in relation to the amount of the oxygen production. There are oxygen enrichment devices using one, two, or multiple cylinders with three or more. In order to produce an oxygen-enriched gas continuously and efficiently from raw material air, a two-cylinder type or multiple-cylinder type of adsorption cylinder as shown in FIG. 1 is preferably used.

As for the compressor 112, a two-head type swing air compressor as well as a rotational air compressor such as screw type, rotary type, scroll type and the like are used as a compressor having a compressing function only or compression and evacuating functions. Either alternating current or direct current may be used as a power source of an electric motor for driving the compressor. Since the compressor 112 may be sources of noise or heat production, the device can be silenced by accommodating the compressor 112 in a compressor box having cooling fan 113.

The oxygen-enriched gas principally composed of the oxygen gas, which was not adsorbed by the adsorption cylinders 131 and 132, flows into a product tank 140 through check valves 128 and 129 provided to prevent backflow of the gas to the adsorption cylinders.

In order to continually produce an oxygen-enriched gas, nitrogen adsorbed on the adsorbents filled in the adsorption cylinders must be desorbed and eliminated. In the desorption step, the adsorption cylinders are connected to an exhaust line by closing the supply valves 121 and 122 and opening the exhaust valves 123 and 124, the adsorption cylinders 131 and 132 are switched from a pressurized state to a state open to the atmosphere, and nitrogen gas adsorbed in the pressurized state is desorbed to regenerate the adsorbents. Noises accompanied with the nitrogen exhaust can be reduced by equipping an exhaust silencer 150 at the end of the exhaust line.

Furthermore, in the desorption step, a purge step is performed to improve the efficiency of nitrogen desorption. In the purge step, the oxygen-enriched gas, which is used as a purge gas, is flowed back from the product side of the adsorption cylinder 131 through the pressure equalizing valve 125 toward the adsorption cylinder 132 which is in an adsorption step. The pressure equalizing valve 125 has orifices 126 and 127 for controlling a flow rate of the purge gas.

Each of the steps is operatively controlled for the time shift performance in the two adsorption cylinders 131 and 132, respectively. While the adsorption step is performed in the adsorption cylinder 131 to produce oxygen, the desorption step is performed in the other adsorption cylinder 132 to regenerate the adsorbent, thus oxygen is continually produced by switching each of the steps.

An oxygen-enriched gas is produced by raw material air and stored in a product tank 140. The oxygen-enriched gas stored in the product tank 140 contains a highly concentrated oxygen-enriched gas which concentration is 95%, for example. While controlling a supply flow rate and a pressure of the oxygen-enriched gas using a flow set means 142 such as a pressure regulating valve 141, the control valve and the like, the oxygen-enriched gas is supplied to a humidifier 145, and the humidified oxygen-enriched gas is supplied to a patient.

For the humidifier 145, a bubbling type or a surface evaporation type humidifiers using water as a moisture source as well as a non-water supply type humidifier can be used. The non-water supply type humidifier supplies and humidifies the oxygen-enriched gas in a dried state by introducing moisture from ambient air using a water permeable membrane module having water permeable membranes, for example, perfluorosulfonic acid-based membrane such as Nafion and the like, polyimide membrane, and polyetherimide membrane.

An ultrasonic-type oxygen concentration/flow rate sensor 144 detects a flow rate and an oxygen concentration of the oxygen-enriched gas to be supplied to a user, and optionally performs a feedback regulation of a rotation rate of the compressor 112 or opening/closing timing of the flow switching valve so as to control oxygen production.

The oxygen enrichment device has a pressure sensor 115 and a relief valve 114 to detect abnormal operation of the compressor or abnormal compression of the adsorption cylinders, and also has a temperature sensor 151 to detect an adsorption temperature in the oxygen enrichment device, thereby performing detection of abnormalities of the device or optimal control of the adsorption and desorption steps.

FIG. 2 is a schematic diagram of opening/closing timing of the flow-channel switching means showing one embodiment of the present invention, which sequentially switches among the supply valves 121 and 122 equipped between the compressor 112 and each of the adsorption cylinders 131 and 132, exhaust valves 123 and 124, and a pressure equalizing valve 125 equalizing a pressure between the adsorption cylinders at the downstream of the adsorption cylinders.

In the pressure swing adsorption-type oxygen enrichment device, as shown in FIG. 2, while the adsorption cylinder 131 is performing the adsorption step, the other adsorption cylinder 132 performs the desorption step. Each of the adsorption and desorption steps are sequentially switched in opposite phases respectively to continually produce oxygen by controlling opening/closing of the supply valves 121 and 122, exhaust valves 123 and 124, and the pressure equalizing valve 125. To improve the efficiency for regenerating the adsorbents, a pressure equalizing step is incorporated to perform energy recovery using pressure shift by communicating between the adsorption cylinder after completion of the purge step (a purge production step and a purge exhaust step) in which a part of the oxygen produced in the adsorption step flows through the pressure equalizing valve 125 to the adsorption cylinder performing the desorption step, the adsorption step or the purge production step and the desorption cylinder after completion of the desorption step or the purge exhaust step. Oxygen can be produced efficiently by performing a steady-state sequence, wherein, while a sequence of the adsorption step, purge production step, pressure equalizing step, desorption step, purge exhaust step, and pressure equalizing step is performed in the adsorption cylinder 131, a sequence of the desorption step, purge exhaust step, pressure equalizing step, adsorption step, purge production step, and pressure equalizing step is performed in the other adsorption cylinder 132.

The purge step is, for example, to extract oxygen from the adsorption cylinder 132 which is producing oxygen in the adsorption step, and to flow a part of the produced oxygen through the pressure equalizing valve 125 to the adsorption cylinder 131 which is depressurizing and exhausting nitrogen in the desorption step, thereby improving the efficiency of the nitrogen desorption and regeneration of the adsorbents. When the length of a purge step is large, the regeneration efficiency of the adsorbents is improved, resulting in an increase in an oxygen concentration of the produced oxygen-enriched gas. When the extracted amount of oxygen is small, an over-adsorption phenomenon occurs in which the adsorbent adsorbs not only nitrogen but also oxygen. Since the concentration of argon gas in the oxygen-enriched gas is increased, the oxygen concentration is decreased. If the length of a purge step is longer, a control for maintaining a high concentration of oxygen can be performed by adjusting the oxygen production.

A purge gas is exhausted to the atmosphere as it is. When the length of an exhaust purge step is too large, the amount of oxygen extracted by the adsorption cylinder 132 is decreased. Furthermore, the concentration of produced oxygen is decreased because of nitrogen breakthrough, depending on the amount of oxygen extracted, resulting in demerits such as lowering the amount of production as the product gas and the like.

The length of a purge step for optimally maintaining the oxygen concentration of the oxygen-enriched gas may differ depending on the temperature of the operational environment of the oxygen enrichment device or the amount of oxygen extracted.

Figure 3:
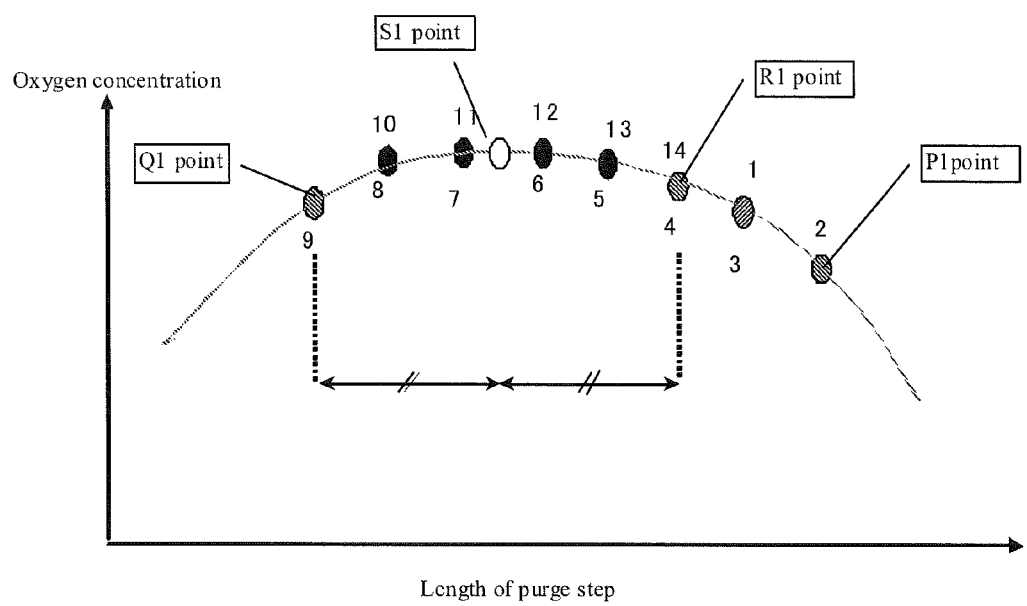
FIG. 3 and FIG. 4 are schematic diagrams according to an example of the oxygen enrichment device of the present invention.

FIG. 3 is a schematic diagram showing control of the length of a purge step of the pressure swing adsorption-type oxygen enrichment device according to one embodiment of the present invention. The control of the length of a purge step is performed as described below.

When the oxygen enrichment device is started, the device is initiated in an adsorption/desorption sequence using the length of a purge step which is set based on the temperature of the oxygen enrichment device (FIG. 3, No. 1). As an optimal sequence changes substantially depending on the device temperature, the device is preferably initiated using a default sequence using the length of a purge step based on the device temperature detected in advance. When a whole of the sequence including changes in the length of an adsorption step or desorption step is controlled, the whole of the sequence becomes imbalanced, requiring a certain time for the oxygen concentration of the produced oxygen-enriched gas to be stabilized. Accordingly, the length of a purge step is controlled in the present invention.

The length of a purge step at the device startup is determined in accordance with the temperature of the ambient air surrounding the device, and the device is initiated at an optimal length of the purge step determined by such temperature. Because of the characteristics of nitrogen adsorption of the adsorbent, when the device is initiated at low temperature below 10° C., the oxygen concentration of the oxygen-enriched gas produced may be increased by setting the length of a purge step at the initial period of startup greater than in the case of startup at normal temperature. Also, to eliminate the effects of the environmental temperature while the device is in operation, even during the change in the set value of the flow rate supplied to a user, the device can be operated at an optimal sequence by changing the length of a purge step to a default length of a purge step corresponding to the temperature in order to respond to the temperature change during operation. Further, even if the environmental temperature during startup fluctuates beyond the specific threshold value due to influence of an air conditioner and the like, control of the length of a purge step may be performed.

The oxygen enrichment device may be used under various environmental conditions, including temperatures ranging from below ice point to high temperature such as nearly 40° C. Fluctuation of the temperature of the usage environment after the device is started causes large change in the nitrogen/oxygen adsorption efficiency of the adsorbents. After the oxygen enrichment device is started in an operational sequence specified at the startup, an optimal operational sequence is determined in accordance with the fluctuation of the oxygen concentration of the oxygen-enriched gas caused by the subsequent environmental change. Accordingly, optimization of the length of a purge step is performed to maximize the oxygen concentration by controlling opening/closing timing of the supply valves and the exhaust valves using the purge step control means. In such control, if the oxygen concentration of the produced oxygen-enriched gas is less than a predetermined specific concentration such as 90%, the length of a purge step is optimized by searching the relationship between the product oxygen concentration and the length of a purge step to improve the product oxygen concentration.

The oxygen concentration of the oxygen-enriched gas immediately before the onset of purge step control is registered as a control reference concentration, and then the length of a purge step is increased by a specific amount (FIG. 3, No. 2). Based on the oxygen concentration detected after a certain duration, the oxygen concentration of the produced oxygen-enriched gas is assessed if the concentration is increased or decreased against the control reference concentration. If the oxygen concentration is increased, the control reference concentration is replaced by the latest concentration and the length of a purge step is further increased. If the oxygen concentration is decreased, the length of a purge step at this point is registered as $P^1$ point (FIG. 3, No. 2). This procedure of increasing the length of a purge step is repeated until a decrease of the oxygen concentration is detected.

When the $P^1$ point is determined, the oxygen concentration at the $P^1$ point is registered as a control reference concentration, and then the length of a purge step is decreased by a specific amount (FIG. 3, No. 3). After a certain duration, the oxygen concentration of the product oxygen-enriched gas is assessed if the concentration is increased or decreased against the control reference concentration. If the oxygen concentration is increased, the control reference concentration is replaced by the latest concentration and the length of a purge step is further decreased. This procedure of decreasing the length of a purge step is repeated until a decrease of the oxygen concentration is detected (FIG. 3, No. 3 to No. 9). If the oxygen concentration is decreased, the length of a purge step at this point is registered as $Q^1$ point (FIG. 3, No. 9).

When the $Q^1$ point is determined, the oxygen concentration at the $Q^1$ point, the latest concentration, is registered as a control reference concentration, and then the length of a purge step is increased by a specific amount. After a certain duration, the oxygen concentration of the produced oxygen-enriched gas is assessed if the concentration is increased or decreased against the control reference concentration. If the oxygen concentration is increased, the control reference concentration is replaced by the latest concentration and the length of a purge step is further increased. This procedure of increasing the length of a purge step is repeated until a decrease of the oxygen concentration is detected (FIG. 3, No. 10 to No. 14). If the oxygen concentration is decreased, the length of a purge step at this point is registered as $R^1$ point (FIG. 3, No. 14).

After the $R^1$ point is determined, an $S^1$ point in FIG. 3, which is the midpoint between the $Q^1$ and $R^1$ points, is determined as an optimal length of a purge step. More specifically, the mean length of the purge steps, namely the $Q^1$ and $R^1$ points, can be determined as the $S^1$ point. At the $S^1$ point, the oxygen-enriched gas having the maximum oxygen concentration can be produced under the environment where the device is in operation.

Figure 4:
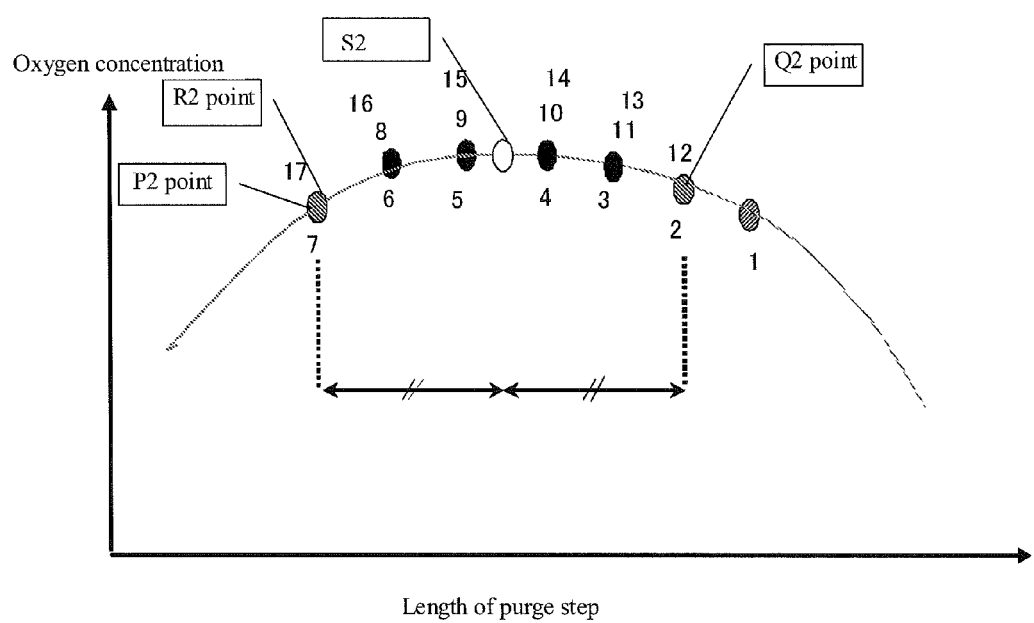

In the above example, control for increasing the length of a purge step is performed at the onset of the control of the length of a purge step. On the contrary, control for decreasing the length of a purge step may also be performed first. As shown in FIG. 4, the oxygen concentration of the oxygen-enriched gas immediately before the onset of the purge step control (FIG. 4, No. 1) is registered as a control reference concentration, and then the length of a purge step is decreased by a specific amount (FIG. 4, No. 2). Based on the oxygen concentration detected after a certain duration, the oxygen concentration of the produced oxygen-enriched gas is assessed if the concentration is increased or decreased against the reference concentration. If the oxygen concentration is increased, the control reference concentration is replaced by the latest concentration and the length of a purge step is further decreased. This procedure of decreasing the length of a purge step is repeated until a decrease of the oxygen concentration is detected (FIG. 4, No. 2 to No. 7). If the oxygen concentration is decreased, the length of a purge step at this point is registered as $P^2$ point (FIG. 4, No. 7).

When the $P^2$ point is determined, the oxygen concentration at the $P^2$ point is registered as a control reference concentration, and the length of a purge step is increased by a specific time (FIG. 4, No. 8). After a certain duration, the oxygen concentration of the produced oxygen-enriched gas is assessed if the concentration is increased or decreased against the reference concentration. If the oxygen concentration is increased, the control reference concentration is replaced by the latest concentration and the length of a purge step is further increased. This procedure is repeated until a decrease of the oxygen concentration is detected (FIG. 4, No. 8 to No. 12). If the oxygen concentration is decreased, the length of a purge step is registered as $Q^2$ point (FIG. 4, No. 12).

When the $Q^2$ point is determined, the oxygen concentration at the $Q^2$ point, the latest concentration, is registered as a control reference concentration, and again the length of a purge step is decreased by a specific amount. After a certain duration, the oxygen concentration of the produced oxygen-enriched gas is assessed if the concentration is increased or decreased against the reference concentration. If the oxygen concentration is increased, the control reference concentration is replaced by the latest concentration and the length of a purge step is further decreased. This procedure is repeated until a decrease of the oxygen concentration is detected (FIG. 4, No. 13 to No. 17). If the oxygen concentration is decreased, the length of a purge step at this point is registered as $R^2$ point (FIG. 4, No. 17).

After the $R^2$ point is determined, an $S^2$ point in FIG. 4, which is the midpoint between the $Q^2$ and $R^2$ points, is determined as an optimal length of a purge step. More specifically, the mean length of the purge steps, namely the $Q^2$ and $R^2$ points, can be determined as the $S^2$ point. Although the $R^2$ point is same as the $P^2$ point in this case, the $S^2$ point is determined not on the midpoint between the $P^2$ and $Q^2$ points but on the midpoint between the $Q^2$ and $R^2$ points, because the length of a purge step relative to the optimal length of a purge step cannot be known at the onset of the purge step control.

At the optimal length of a purge step, the $S^1$ or $S^2$ point, the oxygen enrichment device can produce an oxygen-enriched gas with the maximum oxygen concentration under the environment where the device is in operation.

The control described above is started when the oxygen concentration of the oxygen-enriched gas produced by the adsorption cylinders is less than a predetermined value. However, the control may be performed when the difference between the temperature on start-up and the temperature in operation is greater than a predetermined value due to an air conditioner in a room and the like.

The operation sequence for achieving a maximum oxygen concentration can be determined by detecting an oxygen concentration in the produced gas and setting an optimal length of a purge step precisely. In order to reduce excess oxygen supply, the performance of the air supply means is suppressed, for example, by reducing the rotation rate of the compressor, and by operating the device to maintain the oxygen concentration of the oxygen-enriched gas, for example at 90%, thereby realizing lowering of the power consumption. Furthermore, the oxygen enrichment device is capable of stably supplying an oxygen-enriched gas even if the oxygen production performance is decreased due to deterioration of the operational environment of the device or degradation of the component parts.

The length of a purge step cannot be controlled without any restrictions. If the length of a purge step is set too large, nitrogen breakthrough occurs in the adsorption step. If the length of a purge step is set too small, the efficiency of the adsorbent regeneration is decreased, and thus the oxygen concentration cannot be controlled and maintained at a specified value. It is preferable to preset a range in which the length of a purge step capable of compensating the oxygen concentration control can be varied, and to restrict control of the length of a purge step within this range.

More specifically, in the purge step control, if a limit of the variable range of the length of a purge step is reached without detecting a P point at which the oxygen concentration is decreased compared to the reference concentration, or if, after detecting the P point, a limit of the variable range of the length of a purge step is reached without detecting a Q point at which the oxygen concentration is decreased compared to the reference concentration, the limit of the variable range of the length of a purge step reached is determined as the length of the purge step.

In addition, as a product gas flow rate or temperature conditions also greatly influence the oxygen concentration control, control of stopping or suspending the control of the changing length of a purge step is performed when an oxygen gas flow rate is out of a specific range. When the detected value of the temperature sensor is changed in a specific amount due to change in the environmental temperature, performing the control of changing the length of a purge step is stopped or suspended. Therefore, the oxygen gas concentration when the device is in operation can be compensated.

The purge step control means of the present invention performs control to determine the length of a purge step so as to maximize the product oxygen gas concentration. If the oxygen concentration is more than a necessary concentration, supply airflow rate from the compressor is decreased and the device can be operated in an energy-saving mode, for example, with the oxygen concentration of 90%. On the contrary, if the oxygen concentration is decreased due to degradation of the adsorbents and the like, rotation rate of the compressor is increased and controls of increasing the supply airflow rate and adsorption pressure can be performed concurrently. It is preferable to restrict to perform simultaneously the control for changing supply airflow rate of the compressor, that is, for changing the rotation rate of the compressor and the purge step control for optimizing the length of a purge step.

INDUSTRIAL APPLICABILITY

The oxygen enrichment device of the present invention can be used as a medical oxygen enrichment device for a source of oxygen supply of oxygen inhalation therapy for patients suffering from respiratory system diseases such as asthma, pulmonary emphysema, chronic bronchitis and the like. Also, the oxygen enrichment device can be utilized as a device capable of supplying oxygen stably with low power consumption that is a characteristic of the present invention.

The invention claimed is:
1. A pressure swing adsorption-type oxygen enrichment device comprising:
   first and second adsorption cylinders filled with an adsorbent which selectively adsorbs nitrogen relative to oxygen thereby producing an oxygen-enriched gas;
   a compressor configured to supply raw material air to the first and second adsorption-cylinders;
   a flow-channel switching means for switching flow channels between the compressor and the first and second adsorption cylinders and for repeating an adsorption step, a desorption step, a pressure equalization step and a purge step in a specific timing;
   a flow setting means for supplying the oxygen-enriched gas to a user at a specific flow rate;
   an oxygen concentration sensor configured to detect an oxygen concentration of the oxygen-enriched gas;
   a temperature sensor configured to measure a temperature of the device; and
   a purge step control means for controlling a length of the purge step so as to maximize the oxygen concentration by changing opening/closing timing of the flow-channel switching means, when an output value of the oxygen concentration sensor is lower than a specified value, or the output value of the temperature sensor is out of a specific temperature range,
   wherein the oxygen enrichment device is configured to perform the following steps:
   the adsorption step for supplying compressed air to the first and second adsorption cylinders selectively and extracting an oxygen-enriched gas by sequentially switching the flow channels;
   the desorption step for depressurizing the first and second adsorption cylinders selectively and regenerating the adsorbent;
   the pressure equalizing step for communicating the first and second adsorption cylinders; and
   the purge step for introducing highly concentrated oxygen from the first adsorption cylinder in the adsorption step into the second adsorption cylinder in the desorption step.

2. The oxygen enrichment device according to claim 1, wherein:
the purge step control means is configured to set an oxygen concentration value of the oxygen-enriched gas just before a control for changing a length of the purge step is started as a reference concentration, to perform a first increase control that increases the length of the purge step by a first specific length, and to detect the oxygen concentration value after the first increase control is performed,
the purge step control means is further configured to replace the reference concentration is with an oxygen concentration value after the change of the length of the purge step if the oxygen concentration is increased, and
the purge step control means is further configured to repeat the first increase control until the oxygen concentration is decreased compared to the reference concentration (this point is referred to as $P^1$ point below);
the purge step control means is further configured to set an oxygen concentration value at $P^1$ point as the reference concentration, to perform a decrease control that decreases a length of the purge step by a second specific length, and to detect the oxygen concentration after the decrease control is performed,
the purge step control means is further configured to replace the reference concentration with an oxygen concentration value after the change of the length of the purge step if the oxygen concentration is increased, and
the purge step control means is further configured to repeat the decrease control until the oxygen concentration is decreased compared to the reference concentration (this point is referred to as $Q^1$ point below);
the purge step control means is further configured to set an oxygen concentration value at $Q^1$ point as the reference concentration, to perform a second increase control that increases a length of the purge step by a third specific length and to detect the oxygen concentration after the second increase control is performed,
the purge step control means is further configured to replace the reference concentration with an oxygen concentration value after the change of the length of the purge step if the oxygen concentration is increased, and
the purge step control means is further configured to repeat the second increase control until the oxygen concentration is decreased compared to the reference concentration (this point is referred as $R^1$ point below); and
the purge step control means is further configured to determine a midpoint between the points $Q^1$ and $R^1$ as an optimal length of the purge step.

3. The oxygen enrichment device according to claim 1, wherein:
the purge step control means is configured to set an oxygen concentration value of the oxygen-enriched gas just before changing a length of the purge step is started as a reference concentration, to perform a first increase control that increases the length of the purge step by a first specific length and to detect the oxygen concentration after the control is performed,
the purge step control means is further configured to replace the reference concentration with an oxygen concentration value after the change of the length of the purge step if the oxygen concentration is increased, and
the purge step control means is further configured to repeat the first increase control until the oxygen concentration is decreased compared to the reference concentration (this point is referred as $P^2$ point below);
the purge step control means is further configured to set an oxygen concentration at $P^2$ point as the reference concentration,
the purge step control means is further configured to perform a second increase control that increases the length of the purge step by a second specific length and detect the oxygen concentration after the second increase control is performed,
the purge step control means is further configured to replace the reference concentration with an oxygen concentration value after the change of the length of the purge step if the oxygen concentration is increased, and
the purge step control means is further configured to repeat the second increase control until the oxygen concentration is decreased compared to the reference concentration (this point is referred as $Q^2$ point below);
the purge step control means is further configured to set an oxygen concentration value at the $Q^2$ point as the reference concentration, to perform a decrease control that decreases the length of the purge step by a third specific length and to detect the oxygen concentration after the decrease control is performed,
the purge step control means is further configured to replace the reference concentration is with an oxygen concentration value after the change of the length of the purge step if the oxygen concentration is increased, and
the purge step control means is further configured to repeat the decrease until the oxygen concentration is decreased compared to the reference concentration (this point is referred as $R^2$ point below); and
the purge step control means is further configured to determine a midpoint between points $Q^2$ and $R^2$ as an optimal length of the purge step.

4. The oxygen enrichment device according to claim 2 or 3, wherein the midpoint between points $Q^1$ and $R^1$ or the midpoint between points $Q^2$ and $R^2$ is determined by the mean value of each of the lengths of the purge steps.

5. The oxygen enrichment device according to claim 1, wherein the purge step control means registers an output value of the temperature sensor at a startup or at a change of a set flow rate of the device as a reference temperature, and performs the control by setting the length of a purge step defined by the reference temperature as a default value.

6. The oxygen enrichment device according to claim 5, wherein the purge step control means registers an output value of the temperature sensor at the startup or at the change of a set flow rate of the device as a reference temperature, and resets the length of the purge step to a value defined by an output value of the temperature sensor in advance.

7. The oxygen enrichment device according to claim 2, purge step control means is provided with a preset range in which the length of the purge step is variable, wherein:
if the length of the purge step reaches a limit of preset range without detecting a P point at which the oxygen concentration is decreased compared to the reference concentration, or
if the length of the purge step reaches a limit of the preset range without detecting a Q point at which the oxygen concentration is decreased compared to the reference concentration after detecting the P point,
the attained limit of the preset range is determined as an optimal length of the purge step.

8. The oxygen enrichment device according to claim 1 comprising an oxygen flow rate sensor that detects a flow rate of the oxygen-enriched gas, wherein
the purge step control means performs control for stopping or suspending of executing the change of the length of the purge step when the flow rate of the oxygen-enriched gas is out of a specific range or when the detected value of the temperature sensor is out of a specific range of variation.

9. The oxygen enrichment device according to claim 1, wherein the purge step control means performs control for stopping or suspending of executing the change of the length of the purge step when a value detected by the temperature sensor is out of a specific range of change.

10. The oxygen enrichment device according to claim 1, wherein a compressor control means for controlling the compressor is provided to increase/decrease a supply flow rate based on a detected value of an oxygen concentration of the oxygen enriched gas and to control the oxygen concentration to be maintained at a specified concentration.

11. The oxygen enrichment device according to claim 10, wherein the purge step control means and the compressor control means do not perform respective controls simultaneously.

* * * * *